United States Patent [19]

Palestrant

[11] Patent Number: 5,242,428
[45] Date of Patent: Sep. 7, 1993

[54] APPARATUS FOR WETTING HYDROPHILIC-COATED GUIDE WIRES AND CATHETERS

[76] Inventor: Aubrey Palestrant, 6800 N. 47th St., Paradise Valley, Ariz. 85253

[21] Appl. No.: 771,204

[22] Filed: Oct. 4, 1991

[51] Int. Cl.⁵ ............................................. A61M 5/00
[52] U.S. Cl. ................................................. 604/265
[58] Field of Search ............... 604/265, 268; 184/14, 184/14.1, 15.1, 15.2, 15.3, 16, 17

[56] References Cited

U.S. PATENT DOCUMENTS

| | | | |
|---|---|---|---|
| 3,345,988 | 10/1967 | Vitello | 128/349 |
| 3,606,889 | 9/1971 | Arbiaster | 128/349 |
| 3,721,252 | 3/1973 | Ayella | 134/122 |
| 3,871,358 | 3/1975 | Fukuda et al. | 128/2 |
| 4,063,827 | 12/1977 | Persson | 401/10 |
| 4,534,363 | 9/1985 | Gold | 128/772 |
| 4,705,709 | 11/1987 | Vailancourt | 428/36 |
| 4,749,059 | 6/1988 | Jonnes et al. | 184/15.1 |
| 4,784,647 | 11/1988 | Gross | 604/178 |
| 4,798,593 | 1/1989 | Iwatschenko | 604/164 |
| 4,834,711 | 5/1989 | Greenfield et al. | 604/172 |
| 4,876,126 | 10/1989 | Takemura et al. | 428/35.7 |
| 4,906,237 | 3/1990 | Johansson et al. | 604/268 |
| 4,977,901 | 12/1990 | Ofstead | 128/772 |
| 4,990,357 | 2/1991 | Karakelle et al. | 427/2 |
| 5,002,553 | 3/1991 | Shiben | 606/159 |

Primary Examiner—C. Fred Rosenbaum
Assistant Examiner—Manuel Mendez
Attorney, Agent, or Firm—Cahill, Sutton & Thomas

[57] ABSTRACT

A wetting device includes absorbent material for wetting the hydrophilic coating of a medical guide wire, catheter, or other medical instrument to minimize friction and to facilitate passage of such medical instrument into a patient's body or through another medical instrument. The absorbent material of the wetting device includes a central bore through which a medical instrument is threaded. The absorbent material is supported proximate the point where friction would otherwise result when the hydrophilic coating begins to dry. The absorbent material is wetted, and is preferably made of a deformable, resilient material, allowing the user to squeeze wetting fluid from the absorbent material onto the hydrophilic coating passing therethrough. A porous liner may be included to prevent physical contact between such absorbent material and the medical instrument. The wetting device may include a slit communicating with the central bore to aid in removal of the device after use.

18 Claims, 4 Drawing Sheets

APPARATUS FOR WETTING HYDROPHILIC-COATED GUIDE WIRES AND CATHETERS

BACKGROUND OF THE INVENTION

1. Field of the Invention

The present invention relates generally to medical guide wires and catheters, and more particularly, to an apparatus and method for wetting guide wires, catheters, and other medical instruments of the type having an outer coating of a hydrophilic material or other lubricous coating which provides a slippery, reduced-friction surface when activated by a wetting fluid.

2. Description of the Prior Art

It is well known in the practice of medicine and veterinary science that instruments inserted into the body should have a low coefficient of friction between the instrument and surrounding tissues to facilitate ease of insertion and also to minimize trauma to the tissues surrounding the insertion tract. Such instruments include guide wires and catheters inserted into the vascular system, drainage catheters placed in fluid-secreting organs, such as the kidney and liver, as well as endotracheal and bladder catheters. Similarly, angiographic procedures commonly involve the placement of catheters within blood vessels for treating vascular irregularities. Other examples of tubular instruments which are inserted into the body for diagnosis and treatment include endoscopes for examination of the bowel or urinary tract, as well as ultrasound probes for insertion into blood vessels, bowel, or reproductive organs.

Until recently, instruments of the type described above included a smooth finish applied by carefully polishing the surface in contact with the body, or by application of a substance such as flouro-plastics, silicone or teflon (manufactured by DuPont). Although such polishing technique and surface coatings reduce the amount of friction for such medical instruments, the remaining friction between such instruments and surrounding tissues is still significant.

More recently, newer materials which further decrease the coefficient of friction have been introduced. Such newer materials are known as hydrophilic coatings and include a water soluble polymer applied to the surface of the instrument. Such hydrophilic polymers include cellulosic polymers, polyacrylamide, maleic anhydride polymers, and water soluble nylon. Such hydrophilic coatings are also known in the medical field as hydrogel coatings, and represent one form of a lubricious coating that is activated by a wetting fluid to provide a slippery surface when so activated. Coatings of these materials over medical instruments significantly decrease frictional resistance between such coated medical instruments and the human body. Similarly, such coatings significantly decrease frictional resistance when a coated instrument is passed through another instrument.

The application of various hydrophilic coatings to guide wires, catheters, and other medical instruments is described within U.S. Pat. Nos. 4,705,709 (Vailancourt); 4,798,593 (Iwatschenko); 4,876,126 (Takemura et al.); 4,906,237 (Johansson et al.); 4,977,901 (Ofstead); and 4,990,357 (Karakelle et al.).

Commercial forms of hydrophilic-coated medical guide wires are available from such companies as Meditech, Incorporated of Watertown, Mass., which company markets guide wires of various lengths, thicknesses, and tip configurations under the trademark "Glidewire"; these guide wires are manufactured by Terumo Corporation of Tokyo, Japan and include an outer hydrophilic coating to reduce friction when wet. Such medical guide wires include a super-elastic metallic core for strength and a hydrophilic outer coating for reduced friction. The packaging instructions direct the user to prime the catheter to be passed over the guide wire with heparinized physiological saline before attempting to pass the catheter over the guide wire. The directions further advise that the use of sterilized gauze moistened with physiological saline aids in its handling. Angiographic catheters having hydrophilic outer coatings have also been made commercially available recently.

A disadvantage of such hydrophilic coatings is the requirement that they be continuously wet to maintain their lubricity during use. Furthermore, if such a coated instrument is first wetted and then allowed to dry, the coated surface passes through a phase where the surface becomes somewhat tacky and has a much higher coefficient of friction as compared to the end phase when the coating has completely dried. It is therefore essential to wet those parts of the instrument which lie outside the body before any manipulation can occur.

By way of example, a guide wire is commonly used for inserting and exchanging catheters within the vascular system. The technique for inserting a catheter within the vascular system consists of first establishing a path through the patient's skin into a blood vessel, as by the use of an introducer needle. A guide wire is then inserted through the introducer needle and guided into the blood vessel until the distal tip of the guide wire has advanced to the point of interest. The introducer needle may then be removed, and a catheter is then advanced over the proximal end of the guide wire, through the skin entry point, and along the blood vessel until the distal tip of the catheter reaches the end of the guide wire. The guide wire may then be withdrawn, leaving the catheter in place. If such a guide wire has a hydrophilic coating, it is necessary to wet the guide wire before inserting the proximal end of the guide wire into the distal end of the catheter. However, if the guide wire begins to dry off before the catheter has been fully advanced thereover, the hydrophilic coating can become tacky and resist further advancement of the catheter thereover. Bent-end catheters, such as Simmons catheters and pigtail catheters, are particularly troublesome because of the extra time needed to straighten the curves in order to get the catheter loaded onto the guide wire.

Guide wires are also commonly used for exchanging catheters in the vascular system. The technique for exchange consists of placing the guide wire through a catheter already in the vascular system and removing the catheter from the blood vessel by sliding it over the guide wire and removing the catheter therefrom. The portion of the glide wire that lies outside the patient is wiped with a wet sterile 4×4 gauze pad to remove any residual blood after a catheter is withdrawn thereover. A new catheter is threaded over the guide wire into the vascular system until the distal end of the guide wire is reached and the guide wire is then removed.

If a hydrophilic guide wire is used to perform this procedure, then certain precautions are necessary. When the first catheter is withdrawn during such a catheter exchange operation, the portion of the guide wire that is visible outside the catheter must be wetted to maintain lubricity; otherwise, as the catheter is withdrawn, the frictional force developed between the catheter and guide wire will cause both the catheter and the guide wire to be removed from the blood vessel, resulting in a loss of access to the vascular system.

Once the first catheter has been successfully removed from the guide wire, and the second catheter is to be threaded over the guide wire, the portion of the guide wire lying outside the body must be wetted once again; otherwise, it may be very difficult to thread the second catheter over the guide wire.

In view of the requirement for maintaining the guide wire wet, it is currently necessary for a physician to require the presence of an assistant to keep the guide wire wet while the physician inserts or removes a catheter during an angiographic procedure. For example, during the procedure of inserting a catheter over a guide wire, the physician typically keeps one of his hands at the skin entry point to anchor the guide wire against movement and to prevent bleeding. The physician's other hand usually grasps the distal end of the catheter to advance it over the guide wire. Typically, a nurse or other assistant must take a sterile gauze pad, soak the pad in sterile water, and wipe the guide wire to wet the surface before the physician can advance or retract the catheter. However, it is difficult for the physician and the assistant to coordinate the wiping movement of the gauze pad and the advancement of the catheter so that they are moved at the same rate. The requirement for continued wiping of the guide wire is a nuisance. Moreover, wiping such guide wires with gauze pads can leave a residue which adheres to the surface of such guide wires.

By way of a further example, catheters are often introduced into a blood vessel through a sheath previously placed in a blood vessel or organ. In other cases, catheters are directly introduced through the patient's skin without the use of a sheath. If the catheter includes a hydrophilic coating over its outer surface, the catheter must be wetted prior to insertion through such a sheath or through the patient's skin. Even if the catheter is initially wetted, a delay of only one or two minutes during the insertion procedure can be enough to result in increased friction when the catheter is advanced through the sheath or through the patient's skin, making it much more difficult to pass the catheter into the patient's body.

Devices have been proposed in the past for lubricating, coating, or otherwise engaging catheters. For example, U.S. Pat. No. 3,3456,988 (Vitello) describes a catheter lubricating sac having a lubricating chamber of generally tubular configuration for applying a lubricant to the shaft of a catheter passed therethrough before inserting the catheter into the body. However, such device is not adapted to wet a guide wire over which a catheter is to be passed. Further, such device must be manually supported and is not adapted to be releasably secured to a sheath or to the patient's body for lubricating a catheter as the catheter is being inserted into a patient's body.

U.S. Pat. No. 3,606,889 (Arblaster) discloses a guard accessory for use with a retention type urethral catheter to prevent bacteria from spreading along the exposed portion of the catheter. The device is designed to slide over a portion of the catheter, and includes cushions which wipe against the surface of the catheter. The cushions are porous and are impregnated with an antibiotic ointment which is dispensed along the walls of the catheter. Again, such device is not adapted to wet a guide wire over which a catheter is to be passed. Further, the device is neither designed for, nor capable of, coating the entire length of the catheter as the catheter is being inserted into the patient's body. In addition, the device may not be easily removed from the catheter after the catheter is placed in the body; indeed, it is the purpose of such device to remain fixed on the catheter after the catheter is placed within the body.

U.S. Pat. No. 3,721,252 (Ayella) describes a spray head in the form of a ring coupled to a syringe for rinsing blood from a spring guide wire of the type introduced into blood vessels. The spray head has a central bore through which the spring guide wire is passed. The spray head directs water jets at the spring guide wire as the syringe is depressed. The device is threaded over a guide wire and moved to a point adjacent the entry site and advanced back toward the proximal end while a saline-heparin solution is expelled through the device by a syringe to rinse any blood from the guide wire. The device does not wipe the walls of the spring guide wire, and no means are provided for supporting such device adjacent a catheter, sheath, or adjacent the patient's body. The device is somewhat cumbersome since it requires that one hand of the physician or an assistant be used solely to support and depress the syringe.

U.S. Pat. No. 3,871,358 (Fukuda et al.) describes a guide tube having a passageway through which an endoscope may be passed and includes a liquid-absorbable foam impregnated with a lubricant for lubricating the walls of the endoscope being passed therethrough. However, such a device would not lend itself to use for threading the distal tip of a catheter over a hydrophilic-coated guide wire and is not readily detachable after a medical instrument has been placed within the body.

U.S. Pat. No. 4,784,647 (Gross) describes a device to prevent infection from entering the body along the exposed portion of a urinary tract catheter. A cylindrically shaped block of foam material includes a central bore for receiving the catheter and has a radial slit formed therein to allow the catheter shaft to be inserted into the bore of the foam material. The foam may be impregnated with an antibiotic material that is applied to the wall of the catheter and forms a dressing at the tip of the urethra. The device is not adapted to slide along a catheter to coat the surface with a sliding action; to the contrary, the device includes a circular boss to frictionally engage the shaft of the catheter to prevent displacement of the device once positioned.

U.S. Pat. No. 4,834,711 (Greenfield et al.) describes a medical appliance to lubricate and disinfect urethral catheters or venous catheters. The appliance includes a central conduit through which the catheter extends. A reservoir communicates with the central conduit to introduce lubricant thereto. However, the device is not easily detachable from a catheter that has already been placed in the body, nor are means provided for supporting such a device upon the proximal end of a sheath, nor upon the distal tip of a catheter being threaded over a hydrophilic-coated guide wire.

While the above-described devices are believed to perform useful functions within the applications and uses for which they were designed, it does not appear that any of such devices overcomes the difficulties noted above in conjunction with the use of hydrophilic-coated guide wires, catheters, and other medical instruments.

Accordingly, it is an object of the present invention to provide an apparatus and a method for wetting hydrophilic-coated medical instruments to facilitate insertion of such instruments into the body or through other instruments.

It is another object of the present invention to provide such an apparatus and method which is simple to use, allowing a physician to perform such procedures without the assistance of a nurse or other assistant.

It is a further object of the present invention to provide such an apparatus and method which neither leaves a residue upon, nor adheres to, such hydrophilic-coated surfaces.

Various forms of catheters include hooked or curved distal tips. Such catheters include the Simmons-style, which in its relaxed state, includes a distal tip portion shaped in the form of a Shepherd's crook. Other examples of flexible catheters having curved ends include Cobra tip catheters, and J-Hook catheters and so-called pigtail catheters. Such catheters are commercially available from such companies as Cook Company of Bloomington, Ind. It is often difficult to thread a guide wire into the distal end of such curved-end catheters unless the distal tip of the catheter is first straightened.

Accordingly, it is another object of the present invention to provide such an apparatus and method for wetting a guide wire while simultaneously straightening the distal tip of the catheter to facilitate insertion of the guide wire into the distal end of the catheter.

Still another object of the present invention is to provide such an apparatus and method for wetting a catheter or other medical instrument that includes a hydrophilic outer coating before such instrument is advanced into a sheath, through the patient's skin, or into a patient's orifice.

Yet another object of the present invention is to remove blood or other residue from the guide wire by a wiping action while simultaneously wetting the guide wire to reduce friction.

A further object of the present invention is to provide such a wetting apparatus which can be manufactured inexpensively and easily for disposable use.

A still further object of the present invention is to provide such a wetting apparatus in a form which can be packaged together with various catheters, guide wires, or other medical instruments to provide a ready means for easily and conveniently maintaining the hydrophilic-coated surfaces thereof wet and slippery.

These and other objects of the present invention will become more apparent to those skilled in the art as the description thereof proceeds.

SUMMARY OF THE INVENTION

Briefly described, and in accordance with several preferred embodiments thereof, the present invention relates to a wetting device for continuously wetting a lubricious surface of the type that is activated by a wetting fluid, such as a hydrophilic-coated surface, of a medical instrument as such surface is moved past another surface. For example, such wetting device is adapted to wet a hydrophilic-coated guide wire as the distal end of a catheter is being threaded over the guide wire for insertion into the patient. Similarly, such wetting device is adapted to wet a hydrophilic-coated guide wire as the proximal end of a catheter is being withdrawn over the proximal end of the guide wire. Such wetting device may also be used to wet a hydrophilic-coated guide wire being inserted into a previously placed catheter, as during a catheter exchange operation.

The wetting device of the present invention may also be used to continuously wet the outer lubricious coating of a tubular medical instrument, such as a hydrophilic-coated catheter, as such instrument is inserted into the diaphragm of a larger-diameter sheath or directly into a skin entry point or other orifice of a patient's body.

In one preferred embodiment of the present invention, the wetting device includes absorbent material having a central bore or opening for encircling a guide wire or like medical instrument. A support mechanism is provided for allowing the user to support the absorbent material proximate the distal tip of a catheter that is to be threaded over such guide wire for insertion into the body. Means are provided for wetting the absorbent material, as by soaking or spraying with a wetting fluid, before the catheter is advanced over the guide wire. The user may then advance the absorbent material and the distal tip of the catheter as a unit over the guide wire to continuously wet the portion of the guide wire over which the distal tip of the catheter is to pass. Preferably, the absorbent material is made of a resilient, deformable, sponge-like material for allowing a user to squeeze wetting fluid from the absorbent material as the catheter is advanced over the guide wire.

The absorbent material may include a longitudinal slit communicating with the central bore for allowing the wetting device to be easily removed from the catheter and guide wire after the distal tip of the catheter has advanced into the skin entry point of the patient's body. Alternatively, the central bore or hole within such absorbent material may be of sufficient size to permit the absorbent material to be slid over the proximal end of the catheter.

In a simple form, the support mechanism for supporting the absorbent material proximate the distal tip of the catheter can be merely an extended length of the absorbent material, allowing the distal tip of the catheter to lie within the central bore of the absorbent material. By pinching the absorbent material over the distal tip of the catheter, the user may easily support the absorbent material and the distal end of the catheter for coordinated movement over the guide wire, while simultaneously permitting the user to squeeze wetting fluid from the absorbent material to continuously wet the guide wire.

In another form of the present invention particularly adapted for use with bent-end catheters, the wetting device includes a relatively rigid straightening tube for supporting the distal end of the catheter along the longitudinal axis of the rigid tube. The straightening tube simplifies the engagement of the guide wire with the distal tip of the bent-end catheter and maintains the distal end of the catheter in a straightened configuration while wetting the guide wire to facilitate the passage of the catheter over the guide wire. Preferably, the rigid tube lies coaxial with the central bore within the absorbent material. In addition, the absorbent material may have an enlarged, hollowed-out opening surrounding the end of the rigid tube through which the guide wire is first threaded to allow the user to more easily see the distal tip of the catheter when first threading the distal tip of the catheter onto the guide wire. The rigid tube may also have a slit formed in a side wall thereof for allowing the rigid tube to be removed from the catheter and guide wire after the distal tip of the catheter has passed into the entry point of the patient's body. A liner made of a porous material, or a material having small perforations therein, may be interposed between the absorbent material and the guide wire to prevent direct physical contact between the absorbent material and the guide wire.

Another aspect of the present invention relates to a method of continuously wetting a guide wire having a lubricious coating over which a catheter is being advanced by supporting such a wetting device proximate the distal tip of a catheter for coordinated movement therewith.

Still another aspect of the present invention relates to such a wetting device adapted to facilitate either the withdrawal of a catheter over a guide wire having such a lubricious coating while leaving the guide wire in place, or the insertion of a guide wire having such a lubricious coating into a catheter that is already placed in a patient. In either instance, the absorbent material is supported proximate the proximal end of the catheter, and means are provided for wetting the absorbent material, as by soaking or spraying. The central bore of the wetting device is threaded over the exposed end of the guide wire and supported proximate the proximal end of the catheter, as for example, by releasably connecting the absorbent material support to the proximal end of the catheter through luer lock connectors or the like. The user may then squeeze the absorbent material to emit wetting fluid as the catheter is withdrawn from the patient's body, or alternatively, as the guide wire is advanced into the proximal end of the catheter.

Still another aspect of the present invention relates to the use of such a wetting device in conjunction with a sheath or other oversized tubular passageway through which access to the body may be obtained. In the case of a sheath, a catheter or other medical instrument having such a lubricious coating may be passed into the sheath through a sealing diaphragm at the proximal end of the sheath. The wetting device is supported proximate the proximal end of the sheath, and the catheter or other medical instrument is passed through the central bore of the absorbent material. The user may then continuously wet each portion of the hydrophilic outer coating of the catheter or other medical instrument just prior to such portion being passed into the diaphragm of the sheath.

A further aspect of the present invention relates to a form of the wetting device that is adapted to be positioned directly against the patient's body over the skin entry point into which a catheter or other medical instrument having such a lubricious coating is to be inserted. The wetting device includes a support for supporting the absorbent material proximate the entry point of the patient's body. The distal tip of the catheter is passed through the central opening of the absorbent material before being passed into the entry point of the patient's body. Once again, means are provided for wetting the absorbent material with a wetting fluid for allowing the absorbent material to continuously wet the outer surface of the catheter as the catheter is advanced past the absorbent material and into the patient's body. Preferably, the absorbent material support includes a base having an adhesive applied thereto for releasably securing the absorbent material in position over the skin entry point. The absorbent material may be squeezed as the catheter is advanced therethrough to continuously emit wetting fluid to render the outer surface of the catheter slippery.

DETAILED DESCRIPTION OF THE PREFERRED EMBODIMENTS

Figure 1:
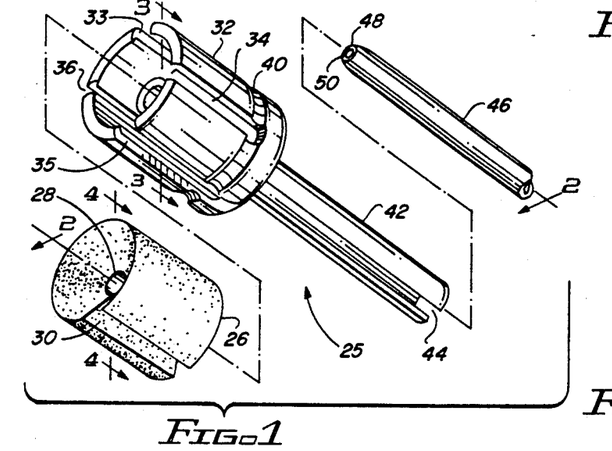
FIG. 1 is an exploded perspective view of a wetting device constructed in accordance with one aspect of the present invention and further illustrates the manner in which the distal end of a catheter may be inserted into such wetting device.
Figure 2:
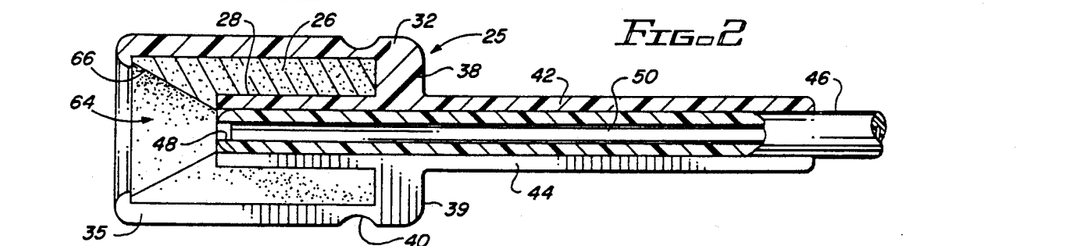
FIG. 2 is a cross-sectional drawing of the wetting device shown in FIG. 1 taken through the plane indicated by lines 2—2 in FIG. 1.
Figure 3:
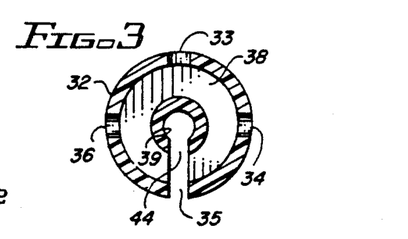
FIG. 3 is a cross-sectional drawing of an absorbent material supporting portion of the wetting device shown in FIG. 1 and viewed through the plane indicated by lines 3—3 within FIG. 1.
Figure 4:
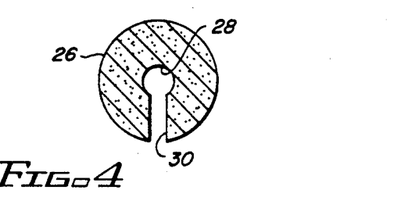
FIG. 4 is a cross-sectional drawing of the absorbent material shown in FIG. 1 viewed through the plane designated by lines 4—4 within FIG. 1.

Within FIGS. 1-4, a first embodiment of a wetting device constructed in accordance with the present invention is shown, wherein such wetting device is generally designated by reference numeral 25. Wetting device 25 includes a generally cylindrical-shaped segment of absorbent material 26 which is preferably made of a resilient, deformable material such as sponge, foam, or the like, which may be rendered sterile for safe usage. As shown best in FIG. 3, absorbent material 26 has a central longitudinal bore 28 formed therein and extending the length thereof. As will be explained in greater detail below, such central bore 28 is of sufficient diameter to permit a guide wire, catheter, or other elongated medical instrument to be passed therethrough. Referring to FIGS. 1 and 4, absorbent material 26 also includes a longitudinal slit 30 extending radially therethrough and communicating with central bore 28. As will be explained in greater detail below, such longitudinal slit facilitates the removal of wetting device 25 from a catheter and/or guide wire.

Still referring to FIGS. 1-4, wetting device 25 also includes a support jacket 32 for supporting absorbent material 26. As shown in FIG. 1, jacket 32 substantially surrounds the curved peripheral walls of absorbent material 26 for firmly supporting such absorbent material. As will be explained in greater detail below, support jacket 32 serves as a means for allowing a user to support absorbent material 26 proximate the distal tip of a catheter as the user advances both the distal tip of the catheter and absorbent material 26 as a unit toward a skin entry point upon the patient's body.

Preferably, support jacket 32 is made of a resilient, deformable material such as plastic for allowing a user to squeeze jacket 32 and thereby squeeze absorbent material 26. As shown in FIGS. 1 and 3, the cylindrical walls of support jacket 32 may include four slots 33, 34, 35, and 36 for allowing the user to more easily compress such cylindrical walls of support jacket 32. The cylindrical walls of support jacket 32 each extend from a front circular wall 38 of support jacket 32. Circular wall 38 has a central bore 39 formed therein for allowing a catheter and guide wire to extend therethrough. Slot 35 extends radially and longitudinally through circular wall 38 to facilitate the removal of wetting device 25 from a catheter and/or guide wire, as will be explained in greater detail below. Such cylindrical walls may be reduced in thickness by a circumferential channel 40 extending around such cylindrical walls adjacent circular wall 38 to render such cylindrical side walls of support jacket 32 further compressible. Support jacket 32 is open at its end opposite circular wall 38 for allowing such cylindrical side walls to flex freely and to facilitate placement of absorbent material 26 into support jacket 32.

As shown in FIGS. 1 and 2, wetting device 25 preferably includes a relatively rigid straightening tube 42, which may, if desired, be made of the same material as support jacket 32 and may be molded integral therewith. Straightening tube 42 is particularly adapted for use with bent-end catheters, such as pigtail catheters, which must be straightened before they can be conveniently threaded over a guide wire. Straightening tube 42 extends coaxially with support jacket 32 and with the central bore 28 of absorbent material 26. Straightening tube 42 has a longitudinally extending slot 44 formed therein, coinciding with slot 35 of support jacket 32, to facilitate removal of wetting device 25 from a catheter and/or guide wire.

Figure 7:
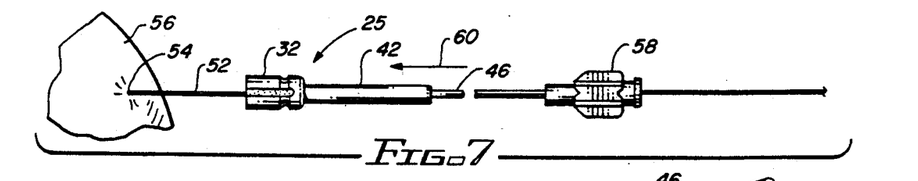
FIG. 7 is a perspective view illustrating a catheter and wetting device being advanced along guide wire toward a skin entry point within the patient's body.

Within FIGS. 1 and 2, the distal end of a catheter 46 is shown, wherein the distal tip is designated 48. Catheter 46 includes at least one through-lumen 50 which may be used for withdrawing or admitting fluids or for other purposes. Lumen 50 may be threaded over a guide wire to safely guide the distal tip 48 of catheter 46 through a skin entry point and along a predetermined insertion tract. Referring briefly to FIG. 7, guide wire 52 is shown extending from a skin entry point 54 of patient's body 56. Guide wire 52 extends fully through lumen 50 of catheter 46 and exits the proximal end 58 thereof. The distal end of catheter 46 is inserted within straightening tube 42 of wetting device 25. The internal diameter of straightening tube 42 is selected to be generally commensurate with the outer diameter of catheter 46. As indicated by arrow 60 within FIG. 7, it is desired to advance catheter 46 along guide wire 52 toward entry point 54.

Figures 8A, 8B, 8C:
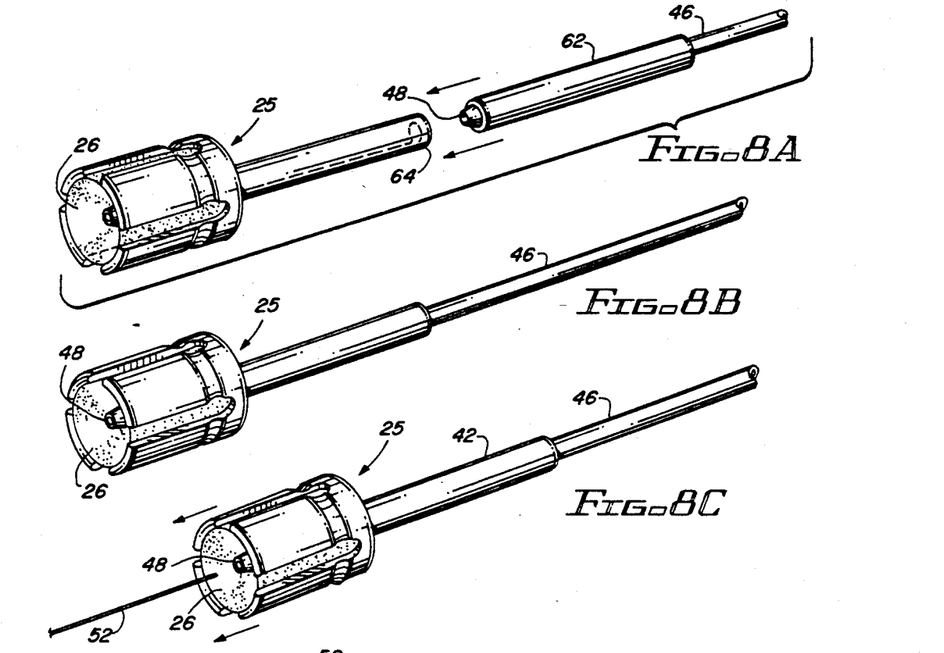
FIG. 8A is a perspective view illustrating a bent-end catheter being advanced through a rigid conduit into a straightening tube portion of the wetting device shown in FIG. 1.
FIG. 8B is a perspective view illustrating the distal tip of a bent-end catheter being fully advanced to the end of the straightening tube of the wetting device.
FIG. 8C is a perspective view of the distal tip of the bent-end catheter being threaded over the proximal end of a guide wire.

The preferred procedure for positioning wetting device 25 proximate the distal tip 48 of catheter 46 is best described by reference to FIGS. 8A, 8B, and 8C. Prior to engaging wetting device 25 with catheter 46, wetting device 25 is first thoroughly wetted by dipping wetting device 25 into a saline-filled bowl, or by squirting saline from a syringe onto absorbent material 26 to allow absorbent material 26 to soak up wetting fluid. Any other wetting means for applying wetting fluid to absorbent material 26 may also be used. Wetting device 25 is then ready for use. Within FIG. 8A, the distal end of bent end catheter 46 is temporarily straightened by sliding a rigid tube 62 toward distal tip 48. Bent-end catheters are often packaged with such a rigid tube 60 for such purpose. Distal tip 48 is then brought adjacent end 64 of straightening tube 42 and advanced into straightening tube 42 until distal tip 48 thereof is just visible through absorbent material 26, as shown in FIG. 8B. As best shown in FIG. 2, the exposed end of absorbent material 26, i.e., the end of absorbent material 26 lying furthest from circular wall 38, includes an enlarged internal opening 64 formed therein commensurate with central bore 28. Internal opening 64 is defined by conical walls 66 which taper inwardly toward an apex aligned with central bore 28. In this manner, the user can easily visualize the distal tip 48 of catheter 46 while leaving distal tip 48 well within absorbent material 26 in order to adequately wet guide wire 52. As shown in FIGS. 1 and 2, straightening tube 42 may extend forward of circular wall 38 into the interior of support jacket 32, if desired, to maintain the distal tip of bent-end catheter in a straightened configuration all the way to the apex of conical walls 66 of absorbent material 26.

Figure 5:
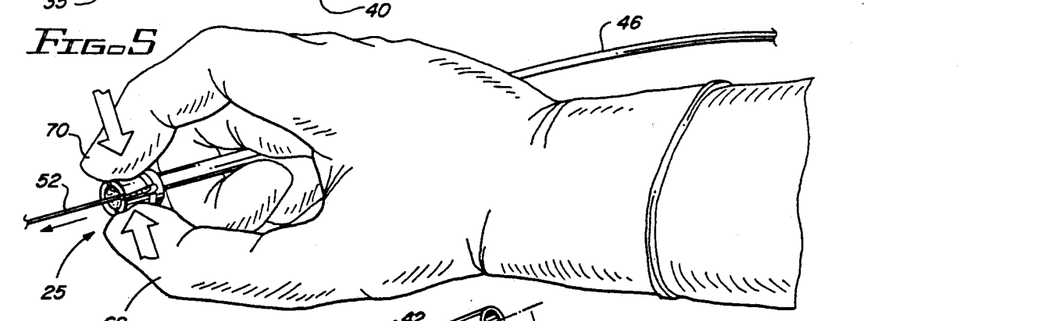
FIG. 5 is a perspective view illustrating the manner in which a physician may, with one gloved hand, simultaneously support the wetting device shown in FIG. 1 as well as the distal end of a catheter while advancing the wetting device and catheter over a guide wire as a unit.

Once the distal tip 48 of catheter 46 is advanced to the position shown in FIG. 8B, the proximal end of hydrophilic-coated guide wire 52 may easily be threaded into lumen 50 of catheter 46 through distal tip 48, as indicated in FIG. 8C. After initially engaging distal tip 48 of catheter 46 over the end of guide wire 52, the physician grasps support jacket 32 of wetting device 25 between the thumb 68 and forefinger 70, as indicated in FIG. 5; the physician curls his other three fingers of the same hand about the distal end of catheter 46. The physician's other hand (not shown) is free to stabilize the guide wire adjacent the skin entry point. As indicated by the arrows shown in FIG. 5, the physician simultaneously squeezes wetting device 25 to exude wetting fluid and pulls both wetting device 25 and the distal end of catheter 46, as a unit with a single hand, along guide wire 52 toward entry point 54. In this manner, wetting fluid continuously exudes over the hydrophilic coating of guide wire 52 just ahead of the distal tip 48 of catheter 46, thereby ensuring that catheter 46 will smoothly glide over guide wire 52.

Figure 6:
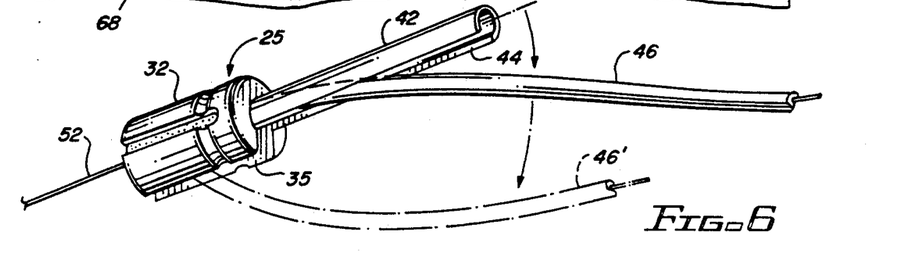
FIG. 6 is a perspective view illustrating the manner by which a catheter and related guide wire may be disengaged from the wetting device via a longitudinal slit formed through such wetting device.

As distal tip 48 approaches near entry point 54 (see FIG. 7), wetting device 25 is preferably removed from catheter 46 and guide wire 52 for allowing the physician to observe the progress of catheter 46 through the entry point. Referring to FIG. 6, catheter 46 (and guide wire 52 extending therein) is pulled through slot 44 of straightening tube 42. As shown in dashed outline within FIG. 6, catheter 46 is then disengaged from absorbent material 26 and support jacket 32 through slit 30 and slot 35, respectively. Wetting device 25 may thereafter be discarded, and distal tip 48 of catheter 46 may then be fully advanced through entry point 54.

Wetting device 25 may be provided in a variety of sizes for use with differently sized catheters, and with guide wires of varying thicknesses. Perhaps as few as three or four differently sized wetting devices would be satisfactory for use with catheters ranging in size from 3 French up to 30 French. Further, wetting device 25 could be conveniently prepackaged with a pigtail catheter or other bent-end catheter, with straightening tube 42 already threaded over the catheter shaft. In this event, the physician would simply advance the wetting device toward the distal end of the catheter whereby the straightening tube of the wetting device would straighten the bent end of the catheter and facilitate threading the proximal end of the guide wire into the distal end of the catheter. The absorbent material of the wetting device could then be soaked with saline to continuously wet the guide wire as the catheter is advanced along the guide wire.

As described above, another aspect of the present invention relates to the use of such a wetting device to aid in the withdrawal of a catheter that has already been placed within a patient, while leaving in place a hydrophilic-coated guide wire over which the catheter is threaded. For example, during a catheter exchange operation, it is necessary to remove a first catheter over such a guide wire before a second catheter can be placed within the patient over the same guide wire. Within FIG. 9, the proximal end 58 of catheter 46 is shown, with hydrophilic-coated guide wire 52 extending therefrom. As indicated by arrow 72 within FIG. 9., the physician desires to slide catheter 46 away from entry point 54 of patient's body 56, while leaving hydrophilic-coated guide wire 52 in place within the patient.

Figures 9, 10A:
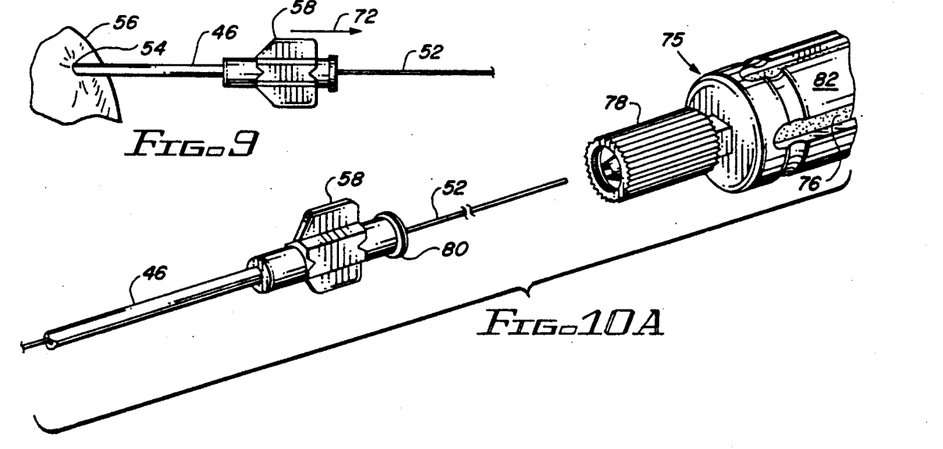
FIG. 9 is a side view of the proximal end of a catheter being withdrawn over a guide wire from a skin entry point of the patient's body.
FIG. 10A illustrates the proximal end of the catheter shown in FIG. 9 and further illustrates an alternate embodiment of a wetting device being threaded over the proximal end of the guide wire.
Figures 10B, 10C:
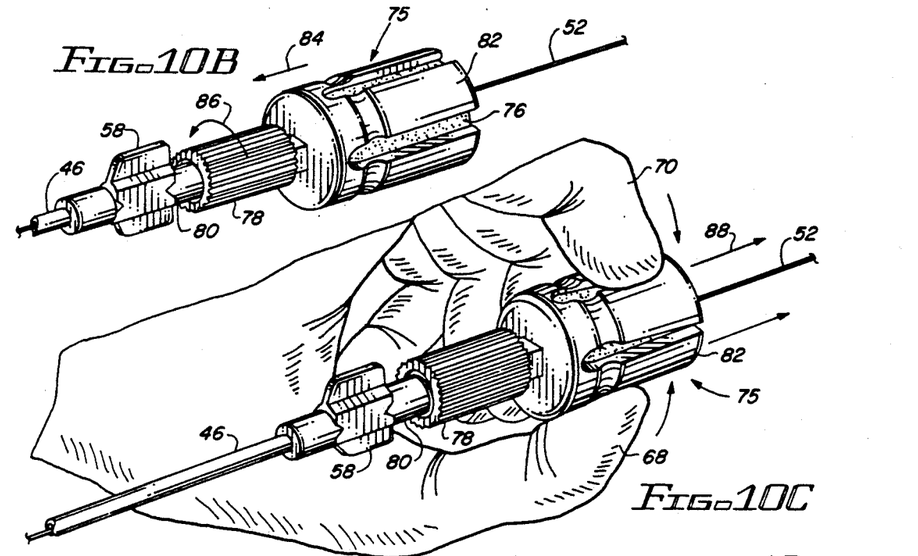
FIG. 10B shows the wetting device of FIG. 10A having been advanced fully to the proximal end of the catheter and being mated with the luer lock connector thereof.
FIG. 10C illustrates a physician's hand squeezing the wetting device to wet the guide wire while simultaneously withdrawing the wetting device and catheter as a unit over the guide wire.

FIGS. 10A, 10B, and 10C illustrates a second embodiment of a wetting device particularly adapted to aid in the removal of catheter 46 over guide wire 52. Wetting device 75 is similar to the wetting device 25 described above. Like wetting device 25, wetting device 75 includes a cylindrical-shaped portion of absorbent material 76, which is partially visible in FIGS. 10A and 10B. Absorbent material 76 is preferably of the same type of construction as absorbent material 26. Wetting device 75 further includes a support jacket 82 having a construction similar to that described above for support jacket 32 for allowing a physician to grasp support jacket 82 and to squeeze wetting fluid from absorbent material 76 supported therein in order to wet the surface of guide wire 52. Unlike wetting device 25, wetting device 75 does not include a straightening tube 42; instead, wetting device 75 includes a male luer lock connector 78 adapted to mate with female luer lock connector 80 typically provided at the proximal end 58 of catheter 46. Male luer lock connector 78 includes a central bore coaxial with the central bore within support jacket 82 and absorbent material 76 for allowing guide wire 52 to be threaded therethrough.

As shown in FIG. 10A, wetting device 75 is initially positioned adjacent the proximal end of guide wire 52 for allowing the central bore of male luer lock connector 78 to be engaged with and threaded over guide wire 52. Before such placement, wetting device 75 is thoroughly wetted with a wetting fluid, such as sterile water or saline. Wetting device 75 is then slid along guide wire 52 until reaching female luer lock connector 80 at the proximal end 58 of catheter 46, as indicated by arrow 84 in FIG. 10B. Wetting device 75 is then releasably secured to proximal end 58 of catheter 46 by twisting the knurled barrel of male luer lock connector 78 over female luer lock connector 80, as indicated by arrow 86 in FIG. 10B. Thereafter, the physician grasps support jacket 82 between thumb 68 and forefinger 70, as shown in FIG. 10C, squeezes support jacket 82 to emit wetting fluid over guide wire 52, and simultaneously pushes wetting device 75, along with catheter 46 secured thereto, toward the proximal end of guide wire 52, as indicated by arrow 88 within FIG. 10C, until the distal tip of the catheter has cleared the proximal end of the guide wire; of course, the physician can stop squeezing absorbent material 76 once the proximal end of the catheter has been advanced beyond the proximal end of guide wire 52.

As mentioned above, a physician may often wish to reinsert a hydrophilic guide wire into a catheter, particularly when the position of the catheter is to be changed or when a new catheter is to be exchanged in place of the catheter that has already been placed within the patient. In this case, wetting device 75 shown in FIGS. 10A-10C may advantageously be used to continuously wet the guide wire as it is being reinserted into the proximal end of the catheter. For such applications, wetting device 75 is first filled with wetting fluid, as by soaking or spraying absorbent material 76 therein. Wetting device 75 is then secured to the proximal end of catheter 46 in the general manner illustrated in FIG. 10B, except that guide wire 52 shown in FIG. 10B is not yet present. After securing wetting device 75 to the proximal end 58 of catheter 46, the distal tip of guide wire 52 is inserted into the open end of wetting device 75 through the central bore formed within absorbent material 76. The distal tip is further advanced through male luer lock fitting 78 and into the proximal end of catheter 46. The physician may then squeeze support jacket 82 to cause wetting fluid to wet the hydrophilic coating of guide wire 52 while advancing guide wire 52 further into catheter 46. Once guide wire 52 is fully inserted within catheter 46, and lies within the patient, catheter 46 may then be withdrawn, leaving guide wire 52 in place, using wetting device 75 in the manner described above.

As mentioned above, it is common for physicians to insert sheaths or other tubular instruments into a patient's body, and to insert catheters or other medical instruments into such sheaths to gain access to the vascular system or to other portions of the body. Such sheaths include a distal end for insertion into a patient's body, as well as an opposing proximal end through which the distal ends of catheters or other instruments may be inserted. Often, such sheaths are equipped with flexible, deformable sealing diaphragms which form a low-pressure seal when no catheter or other instrument is inserted therein, as for preventing excess blood leakage when inserted into the vascular system. Such diaphragms may include a slit or other means by which a catheter or other instrument may be passed through such diaphragms and into the sheath conduit. In this case, the flexible diaphragm wipingly engages the outer walls of the catheter or other instrument being inserted therein to form a low-pressure seal thereabout. Catheters or other instruments to be passes through such a sheath may have hydrophilic coatings applied to their outer surfaces to reduce friction between the catheter and body tissues. However, unless the outer coating of the catheter is kept wet, such catheters can develop significant frictional forces when passing through the flexible diaphragm of the sheath.

Figures 11, 12, 13, 14, 15:
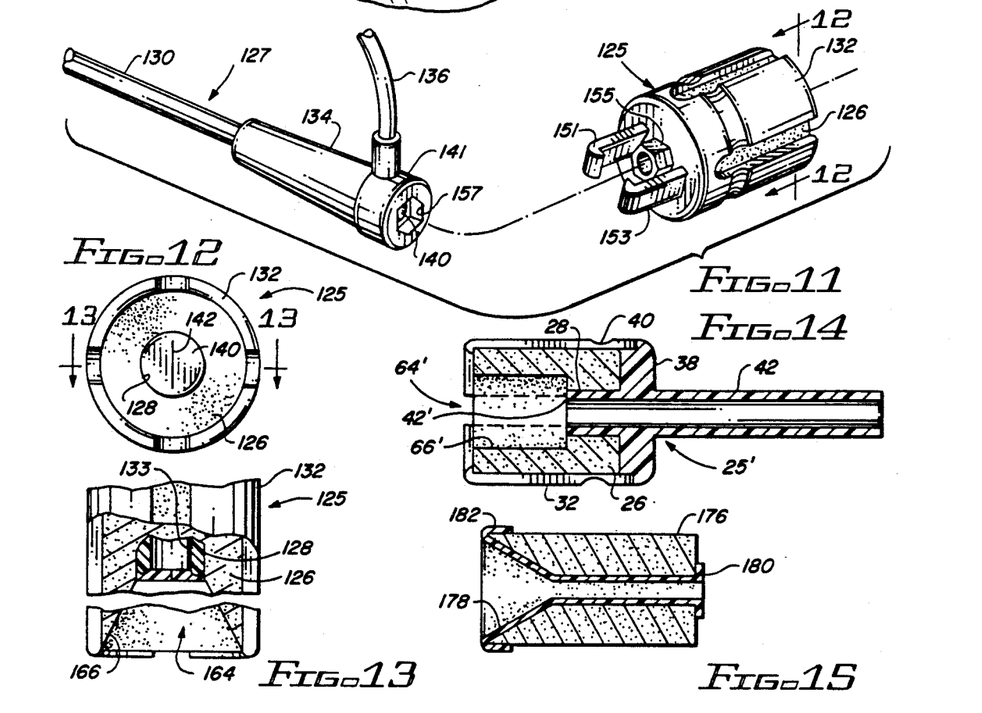
FIG. 11 illustrates an alternate embodiment of the wetting device shown in FIG. 10 and including a different form of connector for connecting such wetting device to the proximal end of an angiographic sheath.
FIG. 12 is an end view of the wetting device shown in FIG. 11 viewed from the plane indicated by lines 12—12 within FIG. 11.
FIG. 13 is a partial cutaway cross-sectional view of the wetting device shown in FIGS. 11 and 12, as viewed through the plane indicated by lines 13—13 within FIG. 12.
FIG. 14 is a cross-sectional view of an alternate embodiment of wetting device of the general type shown in FIG. 1.
FIG. 15 is a further alternate embodiment of a wetting device incorporating a permeable plastic liner for eliminating physical contact between the absorbent material and either the catheter or guide wire.

Shown in FIGS. 11, 12 and 13 is another form of wetting device 125 adapted for use in conjunction with a sheath 127. Sheath 127 includes a tubular conduit 130 having an enlarged proximal end 134. Sheath 127 may include an irrigation tube 136 through which irrigating fluids may be passed into conduit 130. Proximal end 134 of sheath 127 supports a split-seal flexible diaphragm 140. Diaphragm 140, and slit 142 therein, are visible within FIG. 12 through the central bore 144 extending through wetting device 125. Slit 142 is normally urged into a closed sealed position if no catheter or other instrument passes therethrough. However, slit 142 will yield and wipingly engage any instrument inserted through slit 142 to form a seal therearound. Such sheaths are commonly available from medical instrument supply companies.

Wetting device 125 is of a construction similar to that described above for wetting device 25 shown in FIG. 1. Wetting device 125 includes a cylindrical-shaped portion of absorbent material 126 having a central bore 128 extending therethrough. Absorbent material 126 is surrounded by a slotted support jacket 132 as previously described. As shown in FIG. 11, no straightening tube is required, though jacket 132 may include, if desired, an internal liner 133, shown in FIG. 13, which lines central bore 128 of absorbent material 126 to provide a smooth surface over which a catheter or other medical instrument can pass. As indicated in FIG. 13, the open end of wetting device 125 may again include an internal opening 164 concentric with central bore 128 of absorbent material 126. As shown in FIG. 13, absorbent material 126 may be formed to have a conical inward taper to define internal opening 164, wherein the conically tapered walls 166 converge toward an apex lying along the longitudinal axis of the central bore 128, terminating essentially at the end of liner 133.

As shown in FIG. 11, sheath 127 includes an enlarged circular boss 141 at the proximal end 134 thereof. Wetting device 125 may be provided with two or more arms 151 and 153 each including inwardly turned detentes adapted to pass over and releasably engage circular boss 141 of sheath 127. As shown in FIG. 11, wetting device 125 may also include an extending bored neck 155 having a size and shape adapted to be received within the corresponding collar 157 provided within sheath 127. In the example shown in FIG. 11, both the neck 155 and the collar 157 are hexagonal in shape. As will be obvious to those skilled in the art, other releasable fastening mechanisms may be used to releasably secure wetting device 125 to sheath 127.

In use, wetting device 125 is first wetted with wetting fluid, as by soaking or spraying. Wetting device 125 is then releasably secured to the proximal end 134 of sheath 127. The distal tip of a hydrophilic coated catheter, such as catheter 46 shown in FIG. 1, or other hydrophilic-coated medical instrument, is inserted into the open end of wetting device 125. The physician may then squeeze support jacket 132 and absorbent material 126 therein to continuously wet the outer surface of the catheter, while further advancing the distal tip of the catheter through diaphragm 140 and into conduit 130 of sheath 127.

FIG. 14 illustrates an alternate embodiment 25' of the wetting device 25 shown in FIGS. 1-4, and like reference numerals are used within FIG. 14 to identify corresponding components. Unlike the conically shaped opening 64 of wetting device 25 shown in FIG. 2, wetting device 25' of FIG. 14 includes an enlarged cylindrical bore 66' extending coaxial with central longitudinal bore 28 of absorbent material 26. As in the case of wetting device 25, the absorbent material 26 of wetting device 25' is configured to allow a physician to readily see the distal tip of a catheter inserted into such wetting device and protruding from the end 42' of straightening tube 42, while still providing sufficient absorbent material to wet a guide wire over which such catheter tip is being advanced.

FIG. 15 illustrates an alternate embodiment of wetting device adapted to preclude direct physical contact between absorbent material 176 and a guide wire, catheter, or other medical instrument inserted therein. A plastic glove or liner 178, preferably made of a porous plastic, is molded to the contour of the central longitudinal bore and conically shaped open end of absorbent material 176. As shown in FIG. 15, liner 178 may include an enlarged radial flange 180 to abut the flat end of absorbent material 176, and may further include a hooked peripheral rim 182 to extend around the conical end of absorbent material 176, to prevent liner 178 from becoming disengaged from absorbent material 176. Liner 178 allows a tubular instrument to be inserted through absorbent material 176, and allows absorbent material 176 to be squeezed, without allowing direct contact between the instrument and the absorbent material. Preferably, liner 178 is porous, though non-porous plastics having small perforations or slots formed therein could also be used. Liner 178 thereby lessens the possibility that any particles which might become dislodged from absorbent material 176 might adhere to the hydrophilic outer coating of any medical instrument being passed therethrough.

Figures 16, 17, 18, 19, 20, 21, 22, 23:
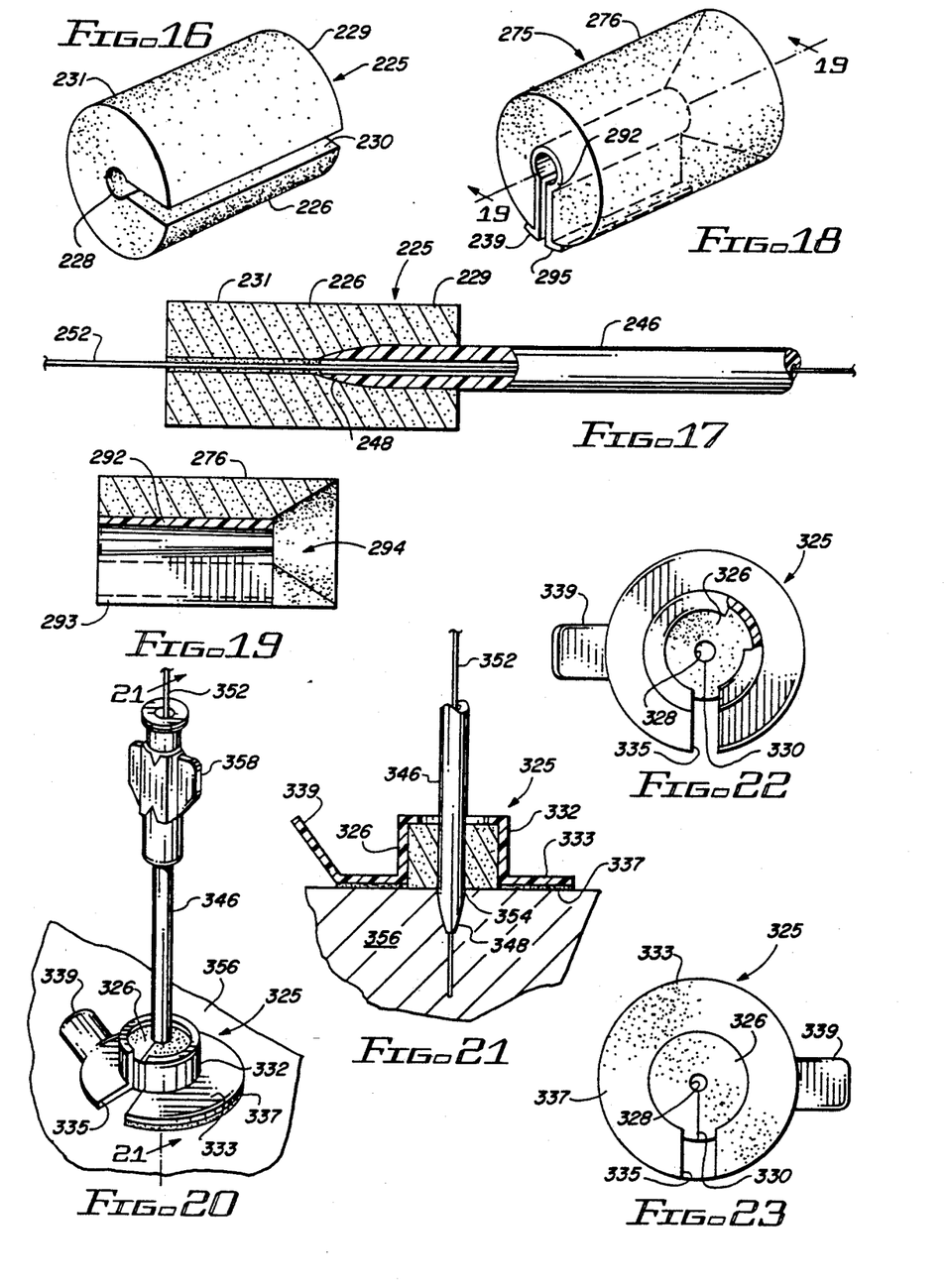
FIG. 16 is a perspective view of absorbent material in the form of a cylinder having a central longitudinal bore and a longitudinal slit for aiding in the removal of such device from a catheter or guide wire.
FIG. 17 is a cross-sectional view of the absorbent material shown in FIG. 16 wherein the distal tip of a catheter is partially inserted within the central bore of such absorbent material to support such absorbent material upon the distal tip of the catheter.
FIG. 18 is an alternate embodiment of a wetting device which includes a winged internal straightening tube.
FIG. 19 is a cross-sectional view of the wetting device shown in FIG. 18 viewed through the plane designated by lines 19—19 within FIG. 18.
FIG. 20 is a perspective view of the proximal end of a catheter extending through an alternate form of wetting device before being advanced into the skin entry point of a patient's body.
FIG. 21 is a cross-sectional view of the catheter and wetting device generally shown in FIG. 20 taken through the plane designated by lines 21—21 within FIG. 20.
FIG. 22 is a partially cut-away top view of the wetting device shown in FIG. 20.
FIG. 23 is a bottom view of the wetting device shown in FIG. 20.

FIGS. 16 and 17 illustrate another embodiment of a wetting device adapted for use in threading a catheter having a relatively straight distal end over a hydrophilic-coated guide wire. In lieu of the support jacket 32 and associated straightening tube 42 shown in FIGS. 1-4, wetting device 225 shown in FIGS. 16 and 17 is formed of an elongated cylindrical absorbent material member 226. Absorbent material member 226 includes a central longitudinal bore 228 of sufficient diameter to permit the distal tip 248 of catheter 246 to be inserted therein. Also, absorbent material 226 is made of sufficient length to allow a physician to support the rightmost (relative to FIG. 17) portion 229 of wetting device 225 upon the distal tip 248 of catheter 246, as by pinching or squeezing such rightmost portion 229 between the physician's palm and curled ring and small fingers. Thus, the rightmost portion 229 of absorbent material 226 serves as a means for supporting absorbent material 226 proximate to distal tip 248 of catheter 246. The physician also squeezes the rightmost portion 231 with his fingers to squeeze water onto guide wire 252. Thus, with one hand, the physician can continuously wet the hydrophilic coating of guide wire 252 while moving his hand toward the skin entry point and moving both wetting device 225 and catheter 246 over guide wire 252. Absorbent material 226 includes a longitudinally extending slit 230 communicating with central bore 228 for allowing easy placement of wetting device about distal tip 248 and guide wire 252, as well as convenient removal therefrom when the skin entry point is reached.

FIGS. 18 and 19 shown another embodiment of a wetting device within the scope of the present invention. Wetting device 275 of FIGS. 18 and 19 is similar in construction to wetting device 225 of FIGS. 16 and 17, but includes a somewhat rigid straightening tube 292 lining the central longitudinal bore of absorbent material 276. Straightening tube 292 is slotted to permit removal of wetting device 275 from a catheter, guide wire or other medical instrument. Such removal is further facilitated by winged radial flanges 293 and 295 which are easily opened and separated from one another to enlarge the slotted channel when removal of wetting device 275 is required. Conical opening 294 is provided within the open end of absorbent material 276 and may be squeezed by the physician to apply wetting fluid over the hydrophilic surface of the guide wire, catheter, or other instrument over which wetting device 275 is passed.

As briefly described above, physicians often pass catheters or other medical instruments directly into a skin entry point or body orifice without the use of a sheath. If the catheter has an outer hydrophilic coating and is not sufficiently wetted, frictional resistance can be met as the physician attempts to pass the catheter through the skin entry point. FIGS. 20-23 illustrate yet another embodiment of a wetting device which may be used by a physician to facilitate passage of a hydrophilic-coated catheter or similar tubular medical instrument into a patient's body through a skin entry point.

Within FIG. 21, the distal tip 348 of catheter 346 is shown after having just advanced beyond skin entry point 354 of patient's body 356; in FIG. 20, catheter 346 is shown after being fully advanced into patient's body 356. As indicated in FIGS. 20 and 21, catheter 346 is guided into the patient's body 356 over guide wire 352. Wetting device 325, shown in FIGS. 20-23, is designed to be releasably secured to patient's body 356 directly over skin entry point 354 for continuously wetting the outer walls of hydrophilic-coated catheter 346 immediately before each portion of such outer walls passes through skin entry point 354.

Wetting device 325 includes a cylindrical-shaped portion of absorbent material 326 having a vertical central bore 328 extending therethrough for wipingly receiving the shaft of catheter 346. A slit 330 is formed within absorbent material 326 to facilitate removal of wetting device 325, if desired, after catheter 346 has been fully advanced into the patient's body. Absorbent material 326 is encircled by and supported by cylindrical support jacket 332 which merges at its lower end with a circular base 333 adapted to rest against patient's body 356. Both support jacket 332 and circular base 333 may have a slot 335 formed therein to facilitate removal of wetting device 325, if desired, after catheter 346 has been fully advanced into the patient's body. As shown in FIGS. 20-23, the upper and lower ends of support jacket 32 are open for allowing catheter 346 to pass through central bore 328 of absorbent material 326.

In use, wetting device is first saturated with wetting fluid, either by soaking wetting device 325 in a bowl of saline, or by spraying or dripping wetting fluid onto absorbent material 326. Wetting device 325 is then applied over the skin entry point and may be manually stabilized by the physician against the patient's body. Assuming that guide wire 352 has already been placed within the patient's body, wetting device 325 may be threaded over the proximal end of guide wire 352 and slid down along guide wire 352 to skin entry point 354, or alternatively, wetting device 325 may be passed around guide wire 352 through slot 335 and slit 330. Catheter 346 is then threaded over guide wire 352 until its distal tip 348 lies just adjacent the upper end of wetting device 325. The physician then gently squeezes support jacket 332 and absorbent material 326 therein while further advancing hydrophilic-coated catheter 346 therethrough to wet the outer walls of the catheter and to activate the hydrophilic coating just before the wetted portions enter through skin entry point 354.

In a preferred embodiment, wetting device 325 has a coating of a medical grade adhesive 337 applied to the lower surface of circular base 333. In use, adhesive 337 is pressed against patient's body 356 to stabilize wetting device 325 in position over skin entry point 354. Tab extends upwardly at an angle from circular base 333 for allowing a physician to easily lift circular base 333 of wetting device 325 to break the adhesive grip of adhesive coating 337 when removal of wetting device 325 is desired.

Those skilled in the art will now appreciate that a wetting device has been described which facilitates the passage of hydrophilic-coated medical instruments through other medical instruments and/or into or out of a patient's body. While the terms "hydrophilic coating" and "wetting" have been frequently used within this written description, it will be appreciated that the present invention is useful with any medical instrument which includes a lubricous surface that is activated by the presence of a wetting fluid, such as water, saline, or another activating fluid; this activating fluid need not be water-based in all instances. In addition, while the terms "guide wire", "catheter", and "sheath" have been frequently used herein, it will be appreciated that the wetting device of the present invention can be used with a variety of elongated, tubular medical instruments that include lubricous coatings which require the presence of a wetting fluid for activation.

Within several of the embodiments of the present invention described above, slits are provided within the absorbent material, and slots are provided within the surrounding support means, to facilitate removal of such devices. Those skilled in the art will appreciate, however, that such slits and slots are not necessary. For example, if the absorbent material is sufficiently resilient, and the central bore therein sufficiently large, then such wetting devices could be simply slid over the proximal end of the catheter or other medical instrument when no longer required.

While the present invention has been described in accordance with several preferred embodiments thereof, the description is for illustrative purposes only and should not be construed as limiting the scope of the invention. Various changes and modifications may be made by those skilled in the art without departing from the true spirit and scope of the invention as defined by the appended claims.

I claim:

1. A wetting device for wetting a medical guide wire to facilitate sliding movement between the guide wire and a catheter, the catheter having an inner lumen extending therethrough for receiving the medical guide wire, the medical guide wire having a lubricous outer surface that is slippery when activated by a wetting fluid, the medical guide wire having opposing first and second ends, the first end of the medical guide wire being adapted to be inserted within the patient's body and the second end of the medical guide wire being adapted to remain external from the patient's body, and the catheter having a distal end intended to lie within the patient's body and an opposing proximal end external from the patient's body, said wetting device comprising in combination:
   a. absorbent material having a central longitudinal bore for substantially encircling the guide wire;
   b. wetting means for wetting said absorbent material; and
   c. support means for allowing a user to support said absorbent material in contact with the guide wire proximate one of the opposing first and second ends of the catheter while sliding the guide wire relative to the catheter and absorbent material, with the guide wire passing through the central longitudinal bore of the absorbent material;
   d. said absorbent material wetting the lubricous surface of a portion of the guide wire just before such portion of the guide wire is slidingly received within the inner lumen of the catheter.

2. The wetting device as recited by claim 1 wherein the catheter has a distal tip to be inserted into a patient's body over the medical guide wire through a skin entry point, wherein said
   support means includes means for allowing a user to support said absorbent material proximate the distal tip of the catheter as the user advances both the distal tip of the catheter and said absorbent material as a unit toward the skin entry point of the patient's body,
   said absorbent material wetting the lubricous surface of said medical guide wire as the distal tip of the catheter is advanced along the medical guide wire toward the skin entry point.

3. The wetting device recited by claim 2 wherein said lubricious surface is a hydrophilic coating, and wherein said wetting fluid includes water.

4. The wetting device recited by claim 3 wherein the catheter includes a proximal end opposite the distal tip thereof, and wherein said absorbent material is made of a resilient, deformable material, and wherein the central longitudinal bore of said absorbent material is of sufficient size to permit said absorbent material to be slid off of the proximal end of the catheter after the distal tip of the catheter has passed into the skin entry point of the patient's body.

5. The wetting device recited by claim 3 wherein said absorbent material is made of a resilient, deformable material, and wherein the central longitudinal bore of said absorbent material is of sufficient size to permit the distal tip of the catheter to be releasably received within the central longitudinal bore of said absorbent material, said support means comprising an extended length of said absorbent material adapted to receive the distal tip of the catheter, whereby a user may pinch a portion of said absorbent material overlying the distal tip of the catheter and thereby support said absorbent material proximate the distal tip of the catheter.

6. The wetting device recited by claim 3 wherein said absorbent material is made of a resilient, deformable material for allowing a user to squeeze water or other wetting fluid therefrom to wet the guide wire.

7. The wetting device recited by claim 3 including liner means substantially covering the central longitudinal bore of said absorbent material for preventing physical contact between said absorbent material and either the guide wire or the catheter while permitting water or other wetting fluid to pass therethrough from said absorbent material to the guide wire.

8. The wetting device recited by claim 3 wherein said absorbent material has a longitudinal slit therein communicating with the central longitudinal bore thereof for allowing said absorbent material to be removed from the guide wire and catheter by passing the guide wire and catheter through said longitudinal slit.

9. The wetting device recited by claim 8 further including a relatively rigid tube having a central bore substantially coaxial with the central longitudinal bore of said absorbent material, the central bore of said rigid tube having an internal diameter commensurate with the outer diameter of the distal tip of the catheter for releasably receiving the distal tip of the catheter and for maintaining the distal end portion of the catheter substantially coaxial with the longitudinal axis of the central bore of said rigid tube.

10. The wetting device recited by claim 9 wherein said rigid tube includes a longitudinal slit coinciding with the longitudinal slit in said absorbent material for allowing said rigid tube to be removed from the guide wire and catheter by passing the guide wire and catheter through the longitudinal slit of said rigid tube.

11. The wetting device recited by claim 9 wherein said absorbent material has first and second opposing ends, and wherein said rigid tube has first and second opposing ends, the first end of being said rigid tube being disposed proximate the second end of said absorbent material, the first end of said absorbent material having an enlarged internal opening formed therein for allowing a user to view the first end of said rigid tube and the distal tip of a catheter received thereby.

12. The wetting device recited by claim 11 wherein the enlarged internal opening formed in the first end of said absorbent material is conically shaped wherein the apex of such cone substantially coincides with the first end of said rigid tube.

13. The wetting device as recited in claim 1, said wetting device serving to facilitate either the removal of a catheter that is threaded over the guide wire or to facilitate the insertion of such guide wire into a catheter, wherein said
  support means includes means for allowing a user to support said absorbent material proximate the proximate end of the catheter, with the guide wire passing through the central longitudinal bore of the absorbent material,
  said absorbent material continuously wetting the medical guide wire when the proximal end of the catheter and the absorbent material are advanced as a unit over the medical guide wire toward the second end of the medical guide wire during withdrawal of the catheter, said absorbent material also serving to continuously wet the medical guide wire when the medical guide wire is advanced into the catheter during insertion of the catheter.

14. The wetting device recited by claim 13 wherein said lubricous surface is a hydrophilic coating, and wherein said wetting fluid includes water.

15. The wetting device recited by claim 14 including liner means substantially covering the central longitudinal bore of said absorbent material for preventing physical contact between said absorbent material and the guide wire while permitting water or other wetting fluid to pass therethrough from said absorbent material to the guide wire.

16. The wetting device recited by claim 14 wherein said support means and said absorbent material are resilient for allowing a user to squeeze said support means and said absorbent material in order to emit wetting fluid from the absorbent material onto the guide wire during either withdrawal of the catheter or during insertion of the guide wire.

17. The wetting device recited by claim 14 wherein the catheter includes a connector at the proximal end thereof, and wherein said support means includes a mating connector for releasably engaging the connector at the proximal end of the catheter in order to support the absorbent material proximate the proximal end of the catheter.

18. The wetting device recited by claim 17 wherein the connector at the proximal end of said catheter and the mating connector of said support means are mating luer lock connectors.

* * * * *